(12) United States Patent (10) Patent No.: US 12,622,641 B2

Ito et al. (45) Date of Patent: May 12, 2026

(54) ELECTROCARDIOGRAMIC MEASUREMENT APPARATUS

(71) Applicant: OMRON HEALTHCARE Co., Ltd., Kyoto (JP)

(72) Inventors: Akito Ito, Kyoto (JP); Reiji Fujita, Kyoto (JP); Yasuhiro Kawabata, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 450 days.

(21) Appl. No.: 17/934,905

(22) Filed: Sep. 23, 2022

(65) Prior Publication Data

US 2023/0012971 A1 Jan. 19, 2023

Related U.S. Application Data

(63) Continuation of application No. PCT/JP2021/007616, filed on Mar. 1, 2021.

(30) Foreign Application Priority Data

Mar. 31, 2020 (JP) ................................. 2020-062860

(51) Int. Cl.
| | |
|---|---|
| *A61B 5/00* | (2006.01) |
| *A61B 5/28* | (2021.01) |
| *A61B 5/318* | (2021.01) |

(52) U.S. Cl.
CPC .............. *A61B 5/6831* (2013.01); *A61B 5/28* (2021.01); *A61B 5/318* (2021.01); *A61B 5/6824* (2013.01); *A61B 2562/043* (2013.01)

(58) Field of Classification Search
CPC ......... A61B 5/6831; A61B 5/28; A61B 5/318; A61B 5/6824
See application file for complete search history.

(56) References Cited

U.S. PATENT DOCUMENTS

| | | | | |
|---|---|---|---|---|
| 2015/0366518 A1* | 12/2015 | Sampson | ............. | A61B 5/7264 |
| | | | | 600/509 |
| 2019/0298265 A1* | 10/2019 | Keating | ............... | A61B 5/6823 |
| 2020/0314184 A1* | 10/2020 | Etemad | .................... | A61B 5/48 |

FOREIGN PATENT DOCUMENTS

| | | | |
|---|---|---|---|
| CN | 104643418 A | | 5/2015 |
| CN | 109700455 A | * | 5/2019 |

(Continued)

OTHER PUBLICATIONS

Definition of Elastic. Merriam-Webster. https://www.merriam-webster.com/dictionary/elastic (Year: 2025).*

(Continued)

*Primary Examiner* — Linda C Dvorak
*Assistant Examiner* — William Mossbrook
(74) *Attorney, Agent, or Firm* — Colson Law Group, PLLC

(57) ABSTRACT

To provide an electrocardiographic measurement apparatus that can prevent a variety of subjects from having discomfort when the apparatus is attached to the subjects. The electrocardiographic measurement apparatus includes: a plurality of electrodes that has a length along a circumferential direction of an upper arm, the length being variable in accordance with a length in the circumferential direction of the upper arm, and detects an electric potential from the upper arm that is brought into contact with the electrodes; and a device body that generates electrocardiographic information based on the electric potential detected by the plurality of electrodes.

4 Claims, 10 Drawing Sheets

(56)                     References Cited

FOREIGN PATENT DOCUMENTS

| JP | 3-107901 | U1 | 11/1991 |
|----|----------|----|---------|
| JP | 6-038938 | A | 2/1994 |
| JP | 2007159644 | A | 6/2007 |
| JP | 2013048767 | A | 3/2013 |
| JP | 5441977 | B2 | 3/2014 |
| JP | 2015534472 | A | 12/2015 |
| JP | 2016131689 | A | 7/2016 |
| JP | 2018-135629 | A | 8/2018 |
| JP | 2019-217043 | A | 12/2019 |
| JP | 2020503096 | A | 1/2020 |

OTHER PUBLICATIONS

Definition of Elastomeric. Merriam-Webster. https://www.merriam-webster.com/dictionary/elastomeric (Year: 2025).*
International Search Report for International Application No. PCT/JP2021/007616, dated Apr. 27, 2021.
International preliminary Report on Patentability for International Application No. PCT/JP2021/007616, dated Dec. 28, 2021.
International Preliminary Report on Patentability Issued for International Application No. PCT/JP2021/007616, dated Dec. 28, 2021.
Office Action issued Nov. 18, 2024 for Chinese Patent Application No. 202180017536.2.

* cited by examiner

ELECTROCARDIOGRAMIC MEASUREMENT APPARATUS

CROSS-REFERENCE TO RELATED APPLICATIONS

This application is the U.S. national stage application filed pursuant to 35 U.S.C. 365(c) and 120 as a continuation of International Patent Application No. PCT/JP2021/007616, filed Mar. 1, 2021, which application claims priority to Japanese Patent Application No. 2020-062860, filed Mar. 31, 2020, which applications are incorporated herein by reference in their entireties.

TECHNICAL FIELD

The present invention relates to an electrocardiographic measurement apparatus used in measurement of a biological signal in accordance with an electric potential generated due to cardiac motion on the surface of a living body.

BACKGROUND ART

An electrocardiographic measurement apparatus is known that detects, as one of biological signals, an electrocardio-graphic signal, which is an electric potential generated due to cardiac motion on the surface of a living body, and generates an electrocardiographic waveform of a subject.

As such an electrocardiographic measurement apparatus, a heartbeat measurement device is known that uses a belt including a belt body to be wound around the chest region of the subject and a plurality of electrodes fixed to an inner surface of the belt body in a longitudinal direction (for example, see Patent Document 1). When the heartbeat measurement device is disposed in a circular pattern, a strap having stretchability and a non-stretchable belt in which the electrodes are disposed are connected with a fitting in a circumferential direction of a band. The electrodes are disposed with the heart sandwiched in detecting an electro-cardiographic signal on the chest region, and thus a large potential difference can be obtained. Therefore, an interval between the electrodes on the non-stretchable belt may be relatively short. As a result, a relatively long stretchable portion can be disposed, and the length of the strap can be easily adjusted.

CITATION LIST

Patent Literature

Patent Document 1: JP 5441977 B

SUMMARY OF INVENTION

Technical Problem

The aforementioned electrocardiographic measurement apparatus may be attached to various limbs (upper limb or lower limb) of the subject by using the band. In this case, it may be troublesome to adjust the length of the band before attaching. Also, when the number of electrodes disposed in the band is increased or the area of each of the electrodes is increased in order to detect a smaller potential difference, it may be difficult to incorporate a portion having stretchability in the circumferential direction of the band. In such a case, after a living body wearable device is attached to a user by the band, the length of the band does not follow an increase in diameter (circumferential length) of a portion on which the living body wearable device is attached, and thus the user may feel discomfort.

An object of the present invention is thus to provide an electrocardiographic measurement apparatus that can pre-vent a variety of subjects from having discomfort when the apparatus is attached to the subjects.

Solution to Problem

According to an aspect of the present invention, an electrocardiographic measurement apparatus is provided that includes: a plurality of electrodes having a length along a circumferential direction of a living body, the length being variable in accordance with a length in the circumferential direction of the living body, the plurality of electrodes being configured to detect an electric potential from the living body that is brought into contact with the plurality of electrodes; and a device body configured to generate elec-trocardiographic information based on the electric potential detected by the plurality of electrodes.

Here, the living body is, for example, an upper arm, a wrist, a chest, a leg, or the like.

According to this aspect, since the length of the plurality of electrodes along the circumferential direction of the living body is variable, the electrocardiographic measurement apparatus can be attached to a variety of subjects, and the various subjects can be prevented from having discomfort when the apparatus is attached to the subjects.

In the electrocardiographic measurement apparatus of the aspect described above, the electrocardiographic measure-ment apparatus is provided in which the plurality of elec-trodes are stretched to vary the length along the circumfer-ential direction of the living body.

According to this aspect, the plurality of electrodes can be formed, for example, in a coil shape or a bellows shape. Further, the plurality of electrodes can be configured such that a plurality of members are movably connected. Fur-thermore, the plurality of electrodes can include a link mechanism.

In the electrocardiographic measurement apparatus of the aspect described above, the electrocardiographic measure-ment apparatus is provided in which a projecting length from a reference position of the plurality of electrodes is variable, and thus the length along the circumferential direction of the living body is variable.

According to this aspect, there is no configuration in which the plurality of electrodes have a variable length. For example, a fixing portion to which the electrode is fixed is configured such that the length of a portion where the electrode protrudes with respect to the fixing portion is variable, and thus the configuration of the electrode can be simplified.

In the electrocardiographic measurement apparatus of the aspect described above, the electrocardiographic measure-ment apparatus is provided in which each of the plurality of electrodes is connected to an insulator, the device body, or a sub-device body to be configured in a circular pattern, and the sub-device body generates electrocardiographic infor-mation based on the electrical potential of the electrode connected to the sub-device body.

According to this aspect, the electrocardiographic mea-surement apparatus is configured in a circular pattern, and thus the electrocardiographic measurement apparatus is eas-ily attached to the living body. Additionally, when the sub-device body is used, the function of the plurality of electrodes to generate electrocardiographic information can be divided into the device body and the sub-device body. Therefore, the size of the device body and the sub-device body can be prevented from being increased.

In the electrocardiographic measurement apparatus of the aspect described above, the electrocardiographic measurement apparatus is provided in which the plurality of electrodes and the insulator or the sub-device body to which each of the plurality of electrodes is connected fix the device body to the living body.

According to this aspect, since a fixture for fixing the electrocardiographic measurement apparatus to the living body is not separately required, the number of components of the electrocardiographic measurement apparatus can be prevented from being increased.

In the electrocardiographic measurement apparatus of the aspect described above, an outer circumferential surface side of the electrode is formed of an insulating portion.

According to this aspect, the plurality of electrodes can be prevented from touching a portion of the living body other than the desired portion, and thus detection accuracy of an electric potential of the living body can be improved.

Advantageous Effects of Invention

The present invention can provide an electrocardiographic measurement apparatus that can be attached to a variety of subjects.

BRIEF DESCRIPTION OF DRAWINGS

Various embodiments are disclosed, by way of example only, with reference to the accompanying schematic drawings in which corresponding reference symbols indicate corresponding parts, in which.

DESCRIPTION OF EMBODIMENTS

First Embodiment

Figure 1:
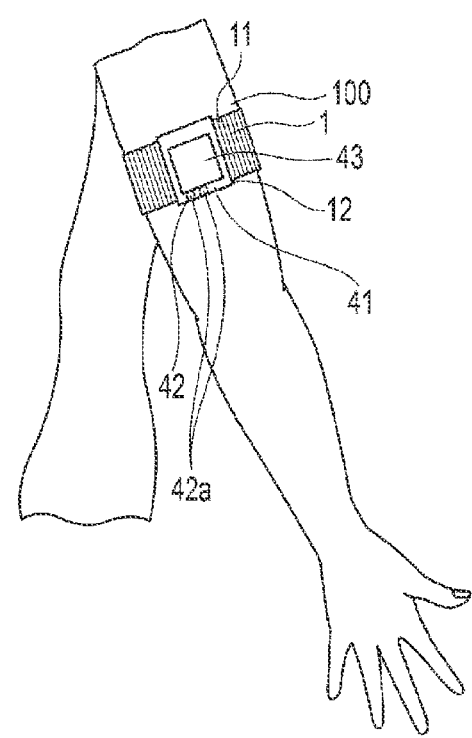
FIG. 1 is an explanatory diagram illustrating a state where an electrocardiographic measurement apparatus according to a first embodiment of the present invention is attached to the upper arm of a subject.
Figure 2:
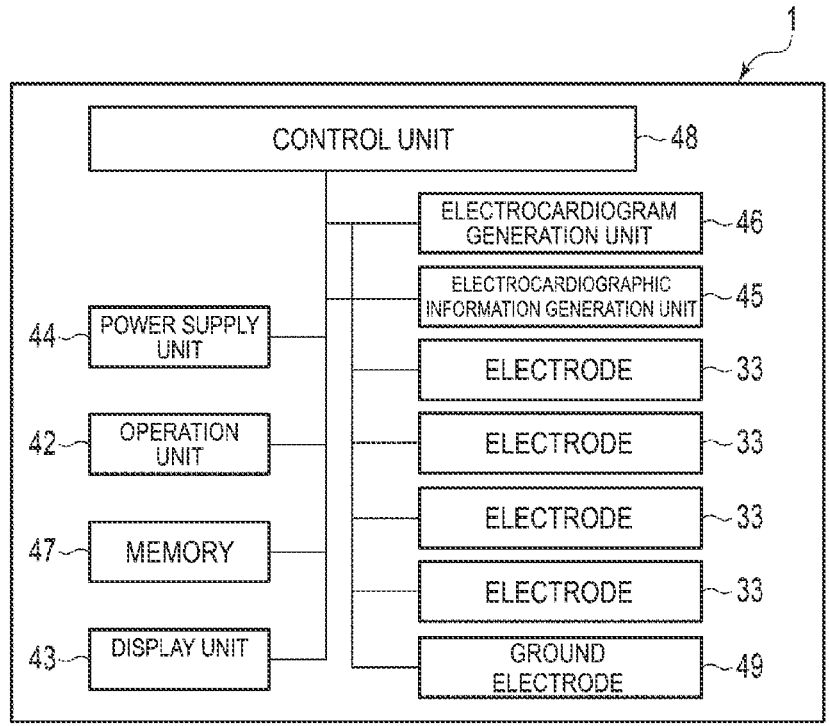
FIG. 2 is a block diagram illustrating the configuration of the electrocardiographic measurement apparatus.
Figure 3:
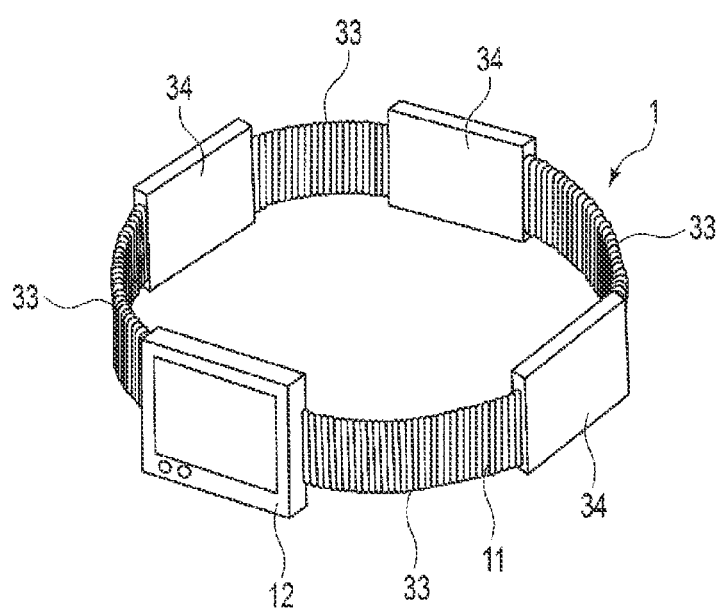
FIG. 3 is a perspective view illustrating the configuration of the electrocardiographic measurement apparatus.
Figure 4:
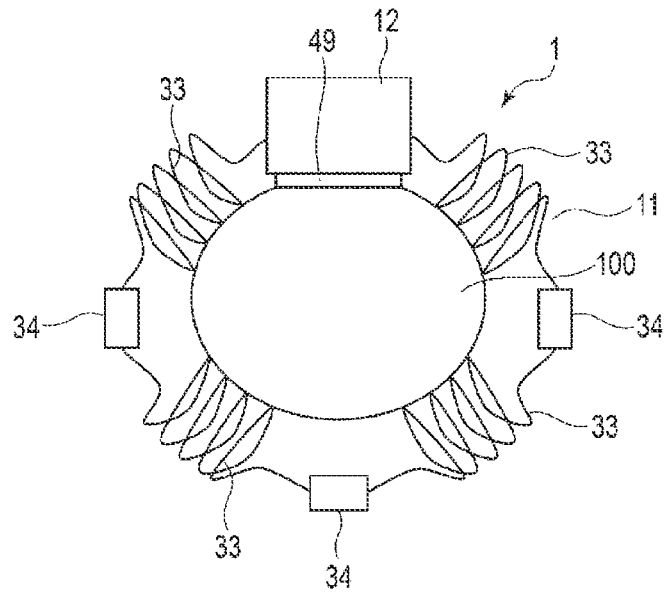
FIG. 4 is an explanatory diagram illustrating a state where the electrocardiographic measurement apparatus is attached to the upper arm.
Figure 5:
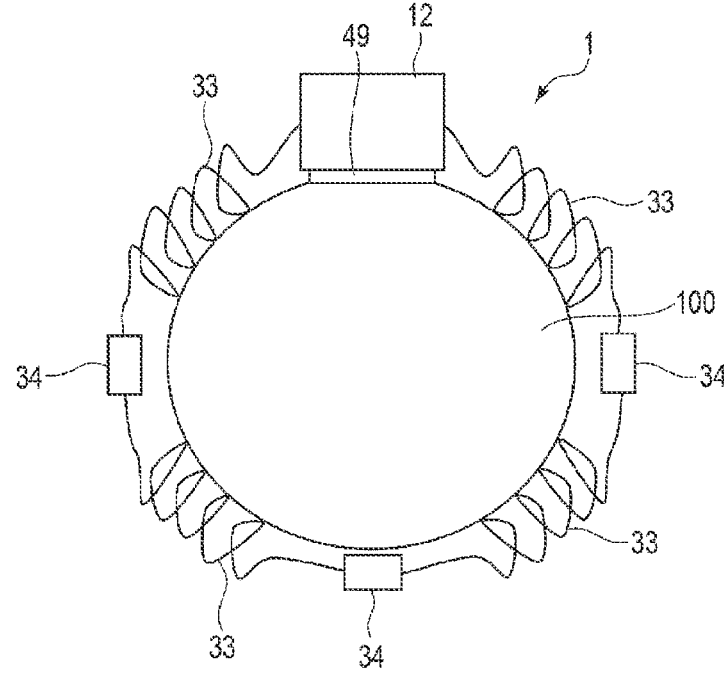
FIG. 5 is an explanatory diagram illustrating a state where the electrocardiographic measurement apparatus is attached to the upper arm.

Hereinafter, an example of an electrocardiographic measurement apparatus 1 according to a first embodiment of the present invention will be described with the use of FIG. 1 to FIG. 5. FIG. 1 is an explanatory diagram illustrating a state where the electrocardiographic measurement apparatus 1 is attached to an upper arm 100 of a subject. FIG. 2 is a block diagram illustrating the configuration of the electrocardiographic measurement apparatus 1. FIG. 3 is a perspective view illustrating the configuration of the electrocardiographic measurement apparatus 1. FIG. 4 is an explanatory diagram illustrating a state where the electrocardiographic measurement apparatus 1 is attached to the upper arm 100. FIG. 4 illustrates a state where the electrocardiographic measurement apparatus 1 is attached to the upper arm 100 of the subject having the shortest circumferential length of the upper arm 100 of the upper arms 100 of a plurality of subjects set as a target for use of the electrocardiographic measurement apparatus 1. FIG. 5 is an explanatory diagram illustrating a state where the electrocardiographic measurement apparatus 1 is attached to the upper arm 100. FIG. 5 illustrates a state where the electrocardiographic measurement apparatus 1 is attached to the upper arm 100 of the subject having the longest circumferential length of the upper arm 100 of the upper arms 100 of the plurality of subjects set as a target for use of the electrocardiographic measurement apparatus 1.

The electrocardiographic measurement apparatus 1 is an electric potential measurement apparatus that is attached to a living body to detect electric potentials at a plurality of points on the skin surface of the living body and generate electrocardiographic information necessary for generating an electrocardiogram based on the detected electric potentials. Note that the electrocardiographic measurement apparatus 1 may generate an electrocardiographic waveform and display the electrocardiographic waveform and may be configured to display information necessary for generating an electrocardiogram and output the information to an external terminal.

As illustrated in FIG. 1 to FIG. 3, the electrocardiographic measurement apparatus 1 includes an attachment portion 11 that includes a plurality of electrodes 33 and is attached to a living body with a portion of the living body disposed inside the attachment portion 11, and a device body 12 that generates electrocardiographic information based on electric potentials detected by the plurality of electrodes 33.

The electrocardiographic measurement apparatus 1 functions as a so-called wearable device including the attachment portion 11 to be attached, for example, to the upper arm 100. FIG. 1 illustrates an example of a state where the electrocardiographic measurement apparatus 1 is attached to the upper arm 100 of the subject.

The attachment portion 11 is fixed to the device body 12 and is formed integrally with the device body 12 in a circular pattern. As illustrated in FIG. 3 to FIG. 5, the attachment portion 11 includes the plurality of electrodes 33 and a plurality of connecting portions 34. Additionally, the attachment portion 11 is configured such that the device body 12 can be fixed to the upper arm 100.

The plurality of electrodes 33 are formed of a conductive material. The plurality of electrodes 33 are configured to be in contact with the upper arm 100 to detect an electric potential of the upper arm 100. The plurality of electrodes 33 has a length along a circumferential direction of the upper arm 100, the length being variable in accordance with a circumferential length of the upper arm 100.

Here, "the length of the plurality of electrodes 33 along the circumferential direction of the upper arm 100 is variable" means that the plurality of electrodes 33 are stretchable or the length of a portion protruding from a reference position of the electrode 33 is variable. The reference position is, for example, the surface of a member to which the electrode 33 is fixed, and is, for example, the connecting portion 34, the device body 12, or the like. The configuration where the plurality of electrodes 33 are stretchable is described as an example in the present embodiment.

The plurality of electrodes 33 are configured to be stretchable. The plurality of electrodes 33 have restorability to return to the original length from the stretched state. The plurality of electrodes 33 are formed, for example, in a stretchable coil shape. Also, the plurality of electrodes 33 are formed, for example, in a flat coil shape. When being stretched, the plurality of electrodes 33 return to the original length by own elasticity. The plurality of electrodes 33 are, for example, four electrodes 33. The plurality of electrodes 33 are fixed to the device body 12 and the connecting portions 34 in the present embodiment. The plurality of electrodes 33 are electrically connected to the device body 12, for example, by wiring or the like. As illustrated in FIG. 3, the surface on the upper arm 100 side of the electrode 33 fixed to the connecting portion 34 is formed, for example, flush with the surface on the upper arm 100 side of the connecting portion 34. The surface on the upper arm 100 side of the electrodes 33 fixed to the device body 12 is formed, for example, flush with the surface on the upper arm 100 side of the device body 12.

The connecting portion 34 is an insulator. The connecting portion 34 insulates and connects the two electrodes 33 adjacent thereto. The plurality of connecting portions 34 are, for example, three connecting portions 34. For example, an end portion of the electrode 33 is integrally formed with the connecting portion 34, and thus the electrode 33 is fixed. Alternatively, the electrode 33 may be fixed to the connecting portion 34 with an adhesive.

Alternatively, the electrode 33 may be detachably and attachably fixed to the connecting portion 34. As an example of this case, an engagement portion is formed at the connecting portion 34, and the end portion of the electrode 33 is formed as an engaged portion, for example, in a hook shape, which can detachably and attachably engage with the engagement portion. In addition, the engagement portion of the connecting portion 34 engages with the engaged portion of the electrode 33, and thus the electrode 33 is detachably and attachably fixed to the connecting portion 34. In another example, by using a magnet, the electrode 33 may be detachably and attachably fixed to the connecting portion 34. For example, a magnet is disposed on at least one of the connecting portion 34 or the electrode 33. A metal or a magnet that can be fixed to the magnet is disposed on the other one.

Both end portions of the attachment portion 11 configured as just described are formed of, for example, two of the electrodes 33. The two electrodes 33 forming the both end portions of the attachment portion 11 are fixed to the device body 12.

The circumferential length of the attachment portion 11 in a state where the plurality of electrodes 33 are not stretched is set to a length that is shorter than the shortest length of the circumferential length of the upper arms 100 of the plurality of subjects set as a target for use of the electrocardiographic measurement apparatus 1. In other words, as illustrated in FIG. 4, in a state where the electrocardiographic measurement apparatus 1 is attached to the upper arm 100, the circumferential length of which is shortest, the plurality of electrodes 33 stretch along the circumferential direction of the upper arm 100. The amount of stretch of the plurality of electrodes 33 in such a state is the amount of stretch that enables the electrocardiographic measurement apparatus 1 to be fixed to the upper arm 100 by tightening force that is generated by restoring force of the plurality of electrodes 33.

Also, the circumferential length of the attachment portion 11 in a state where the plurality of electrodes 33 are maximally stretched is set to a length that is equal to or longer than the longest length of the circumferential lengths of the upper arms 100 of the plurality of subjects set as a target for use of the electrocardiographic measurement apparatus 1. In other words, the electrocardiographic measurement apparatus 1 can be fixed to the upper arm, the circumferential length of which is longest.

As just described, the electrocardiographic measurement apparatus 1 can be fixed by the attachment portion 11 to each of the upper arms 100 of the plurality of subjects set as a target for use of the electrocardiographic measurement apparatus 1.

As illustrated in FIG. 1 and FIG. 2, the device body 12 includes a case 41, an operation unit 42, a display unit 43, a power supply unit 44, an electrocardiographic information generation unit 45, an electrocardiogram generation unit 46, a memory 47, and a control unit 48. Further, the device body 12 includes a communication unit that transmits and receives information with an external terminal. Note that the communication unit transmits and receives information with an external terminal wirelessly and/or in a wired manner. Furthermore, the device body 12 includes, for example, a ground electrode 49.

The case 41 houses a portion of the operation unit 42, a portion of the display unit 43, the electrocardiographic information generation unit 45, the electrocardiogram generation unit 46, the memory 47, and the control unit 48. Additionally, the case 41 exposes a portion of the operation unit 42 and a portion of the display unit 43 from the outer surface.

The operation unit 42 is configured to receive an instruction input from a user. For example, the operation unit 42 includes a plurality of buttons 42a and a sensor that detects operations of the buttons 42a. Note that the operation unit 42 may include a touch panel of a pressure sensitive type, a capacitance type, or the like, a microphone that receives an instruction by sound, or the like, which are disposed on the case 41, the display unit 43, or the like. When operated by the user, the operation unit 42 converts the instruction into an electrical signal and outputs the electrical signal to the control unit 48.

The display unit 43 is electrically connected to the control unit 48. The display unit 43 is, for example, a liquid crystal display (LCD) or an organic electro luminescence display (OELD). The display unit 43 displays date and time, electrocardiographic information, an electrocardiographic waveform, or the like in accordance with a control signal from the control unit 48. Note that, in a case where the electrocardiographic measurement apparatus 1 is used in a biological information measurement device that displays a blood pressure value, the display unit 43 may display a variety of information including measurement results of blood pressure values such as systolic blood pressure and diastolic blood pressure, a heart rate, or the like.

The power supply unit 44 is a power source. The power supply unit 44 is, for example, a rechargeable battery such as a lithium ion battery. The power supply unit 44 is electrically connected to the control unit 48. As a specific example, the power supply unit 44 supplies power to the control unit 48. The power supply unit 44 supplies power for drive to the control unit 48, and via the control unit 48 to the operation unit 42, the display unit 43, the electrocardiographic information generation unit 45, the electrocardiogram generation unit 46, and the memory 47.

The electrocardiographic information generation unit 45 is electrically connected to the plurality of electrodes 33 and the ground electrode 49. The electrocardiographic information generation unit 45 calculates a potential difference from electric potentials detected by the plurality of electrodes 33 and generates electrocardiographic information.

The electrocardiogram generation unit 46 is electrically connected to the electrocardiographic information generation unit 45. The electrocardiogram generation unit 46 generates information of an electrocardiogram based on the electrocardiographic information generated by the electrocardiographic information generation unit 45. The information of the electrocardiogram may include electrocardiographic waveforms.

The electrocardiographic information generation unit 45 and the electrocardiogram generation unit 46 as just described are processing circuits that can respectively execute, for example, functions of the electrocardiographic information generation unit 45 and the electrocardiogram generation unit 46. The electrocardiographic information generation unit 45 and the electrocardiogram generation unit 46 are electrically connected to the control unit 48. Note that the control unit 48 includes the processing circuits of the electrocardiographic information generation unit 45 and the electrocardiogram generation unit 46 and executes a program stored in the memory 47 and thus may perform the functions of the electrocardiographic information generation unit 45 and the electrocardiogram generation unit 46.

Also, for example, the electrocardiographic information generation unit 45 or the electrocardiogram generation unit 46 may include a low pass filter, an amplifier, and an analog/digital converter. For example, unnecessary noise components are removed from a signal of the potential difference by the low pass filter, and the signal is amplified by the amplifier and then converted into a digital signal by the analog/digital converter.

The memory 47 includes a solid state drive (SSD), a random access memory (RAM), a read only memory (ROM), and the like. The memory 47 stores programs necessary for executing a variety of control processing. Further, the memory 47 stores the detected electrocardiographic signal, the generated electrocardiographic information and electrocardiogram information, and the like. Furthermore, for example, the memory 47 stores these pieces of information in a chronological order.

The control unit 48 includes one or a plurality of processors. The control unit 48 is formed of one or more processing circuits. The control unit 48 is, for example, a central processing unit (CPU). The control unit 48 causes the entire operation and predetermined operation (function) of the electrocardiographic measurement apparatus 1 to be executed based on the programs stored in the memory 47. The control unit 48 executes the predetermined operation, analysis, processing, or the like according to the read program. The control unit 48 controls operation of the operation unit 42, the display unit 43, the electrocardiographic information generation unit 45, and the electrocardiogram generation unit 46, transmits/receives a signal, and supplies power.

The ground electrode 49 is fixed, for example, to the surface on the upper arm 100 side of the case 41. The ground electrode 49 is electrically connected to the electrocardiographic information generation unit 45.

An example of attachment of the electrocardiographic measurement apparatus 1 configured as just described to the upper arm 100 of the subject will be described. In a case where the electrocardiographic measurement apparatus 1 is configured such that the electrodes 33 are fixed to the connecting portions 34, the subject inserts the arm from fingertips into the attachment portion 11. Then, the subject moves the attachment portion 11 to the upper arm 100.

The plurality of electrodes 33 stretch and contract along the circumferential direction of the upper arm 100 in accordance with the circumferential length of the upper arm 100 of the subject. Furthermore, by having restoring force to return the attachment portion 11 from the stretched state, the attachment portion 11 tightens the upper arm 100. The electrocardiographic measurement apparatus 1 is fixed to the upper arm 100 of the subject by such tightening force.

In a case where the electrocardiographic measurement apparatus 1 is configured such that the electrode 33 is detachably and attachably fixed to the connecting portion 34, the subject releases, for example, fixation between one electrode 33 of the plurality of electrodes 33 and the connecting portion 34.

Next, the subject wraps the attachment portion 11 and the device body 12 around the upper arm 100. Next, the subject fixes the electrode 33 and the connecting portion 34 that are released from the fixation therebetween. In this case, the subject stretches the plurality of electrodes 33 by pulling the attachment portion 11 in accordance with the upper arm 100. The electrode 33 and the connecting portion 34 that are released from the fixation therebetween are fixed, and thus the attachment portion 11 and the device body 12 are configured in a circular pattern. The attachment portion 11 and the device body 12 are configured in a circular pattern, and thus the upper arm 100 is tightened by the attachment portion 11 with the restoring force of the plurality of electrodes 33. The upper arm 100 is tightened by the attachment portion 11, and thus the electrocardiographic measurement apparatus 1 is fixed to the upper arm 100.

When the electrocardiographic measurement apparatus 1 is fixed to the upper arm 100 as just described, the subject operates the operation unit 42, and thus the control unit 48 controls each configuration and detects an electrocardiographic signal via the two electrodes 33. Then, the electro-cardiographic information generation unit 45 generates elec-trocardiographic information from the electrocardiographic signal, and the electrocardiogram generation unit 46 gener-ates electrocardiogram information from the electrocardio-graphic information. The control unit 48 allows the memory 47 to store the electrocardiographic information and the electrocardiogram information and allows the display unit 43 to display information such as a date and time and an electrocardiogram. Also, the control unit 48 may control the communication unit to transmit a variety of information such as the date and time, the electrocardiographic infor-mation, and the electrocardiogram information to an exter-nal terminal.

In the electrocardiographic measurement apparatus 1 con-figured as just described, the plurality of electrodes 33 is configured such that the length is variable along the circum-ferential direction of the upper arm 100 in accordance with the circumferential length of the upper arm 100. Therefore, the electrocardiographic measurement apparatus 1 can be attached to the upper arms 100 of a variety of subjects and can prevent the various subjects from having discomfort when the apparatus is attached to the subjects.

Additionally, the plurality of electrodes 33 have restorability to return from the stretched state, and thus the device body 12 can be fixed to the upper arm 100 by the attachment portion 11. As a result, since a fixture for fixing the attachment portion 11 and the device body 12 to the upper arm 100 is not separately required, the number of components of the electrocardiographic measurement appa-ratus 1 can be prevented from being increased.

Figure 6:
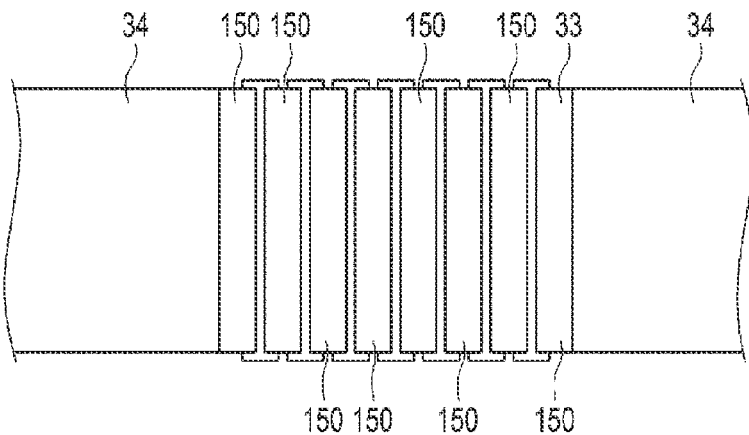
FIG. 6 is an explanatory diagram illustrating the configuration of a major portion of the electrocardiographic measurement apparatus of a modified example.
Figure 7:
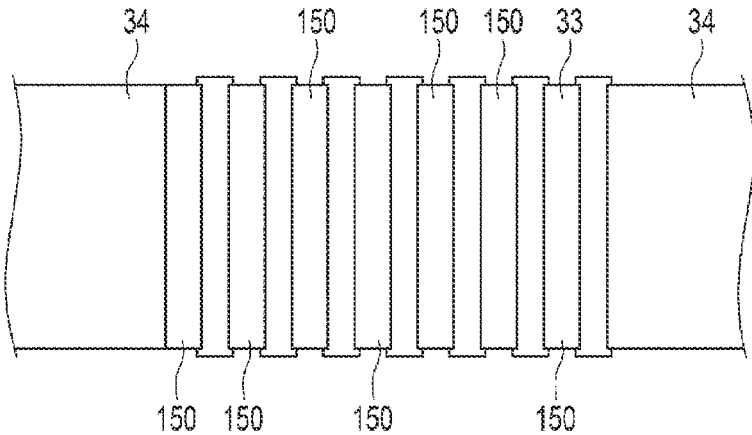
FIG. 7 is an explanatory diagram illustrating the configuration of the major portion.

Note that in the example described above, the configura-tion where the electrodes 33 are formed in a coil shape is described as an example, but is not limited thereto. In other examples, as in a modified example illustrated in FIG. 6 and FIG. 7, the electrode 33 includes, for example, a plurality of conductive plate members 150 that are long in one direction, and the plurality of plate members 150 may be configured to be movably connected by a spring or the like. The movement referred to here is movement in a direction to widen the interval between the two adjacent plate members 150 and movement in a direction to narrow the interval between the two adjacent plate members 150. The plurality of plate members 150 are movably connected as just described, and thus the plurality of electrodes 33 are configured to be stretchable. Additionally, the plurality of electrodes 33 may have restoring force to return from the stretched state. FIG. 6 is an explanatory diagram illustrating one electrode 33 and a portion of the two connecting portions 34 connected to the electrode 33. FIG. 7 is an explanatory diagram illustrating a state where the electrode 33 illustrated in FIG. 6 is stretched.

Figure 8:
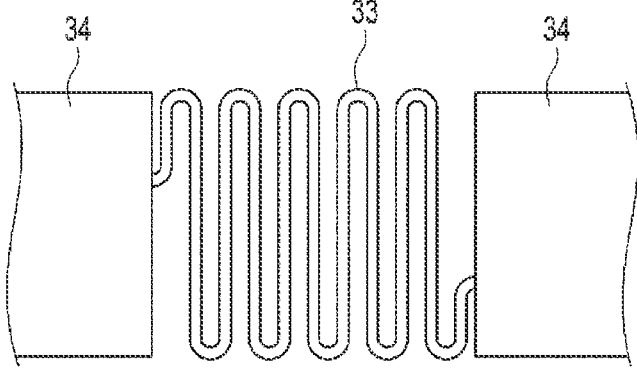
FIG. 8 is an explanatory diagram illustrating the configuration of a major portion of the electrocardiographic measurement apparatus of a modified example.
Figure 9:
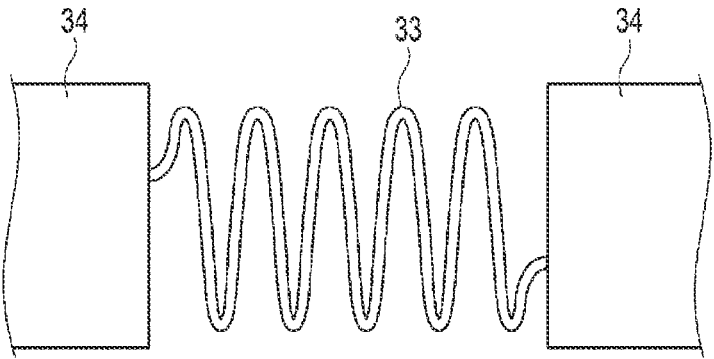
FIG. 9 is an explanatory diagram illustrating the configuration of the major portion.

Also, the electrodes 33 may be formed of a conductive material into a bellows shape as in another modified example illustrated in FIG. 8 and FIG. 9. The bellows-shaped electrode 33 may have restoring force to return from the stretched state. FIG. 8 is an explanatory diagram illus-trating one electrode 33 and a portion of the two connecting portions 34 connected to the electrode 33. FIG. 9 is an explanatory diagram illustrating a state where the electrode 33 illustrated in FIG. 8 is stretched.

Figure 10:
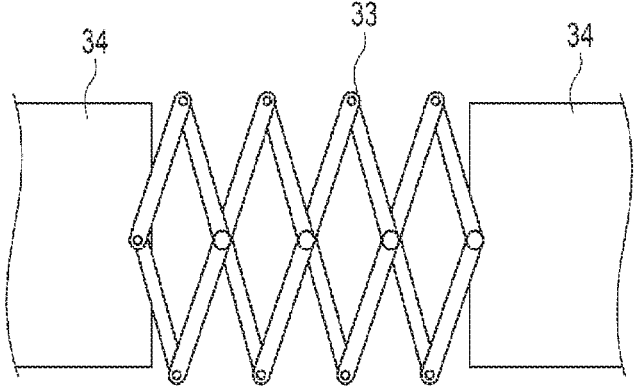
FIG. 10 is an explanatory diagram illustrating the configuration of a major portion of the electrocardiographic measurement apparatus of a modified example.
Figure 11:
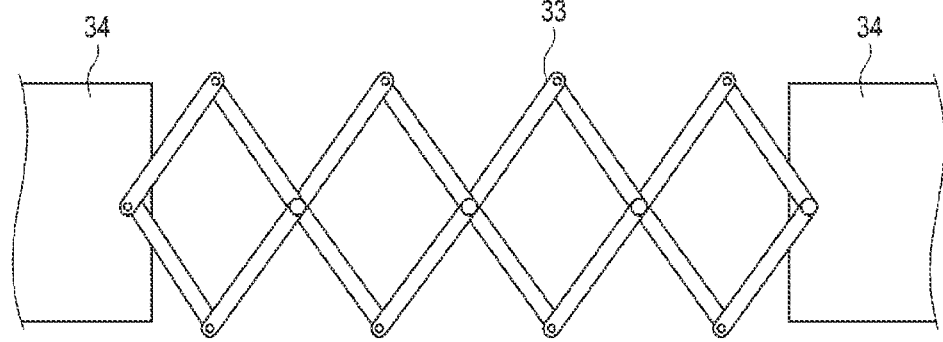
FIG. 11 is an explanatory diagram illustrating the configuration of the major portion.

Also, in the aforementioned embodiments, the configu-ration where the electrode 33 has restoring force to return to the original length when stretched is described as an example, but is not limited thereto. In other examples, the electrode 33 may be configured without having the restoring force to contract from the stretched state. As such an example, the electrode 33 may include, for example, a stretchable link mechanism as in a modified example illus-trated in FIG. 10 and FIG. 11. FIG. 10 is an explanatory diagram illustrating the electrode 33 and a portion of the two connecting portions 34 connected to the electrode 33. FIG. 11 illustrates the electrode 33 and a portion of the two connecting portions 34 connected to the electrode 33 and illustrates a state where the electrode 33 is more stretched than the state illustrated in FIG. 10.

Second Embodiment

Figure 12:
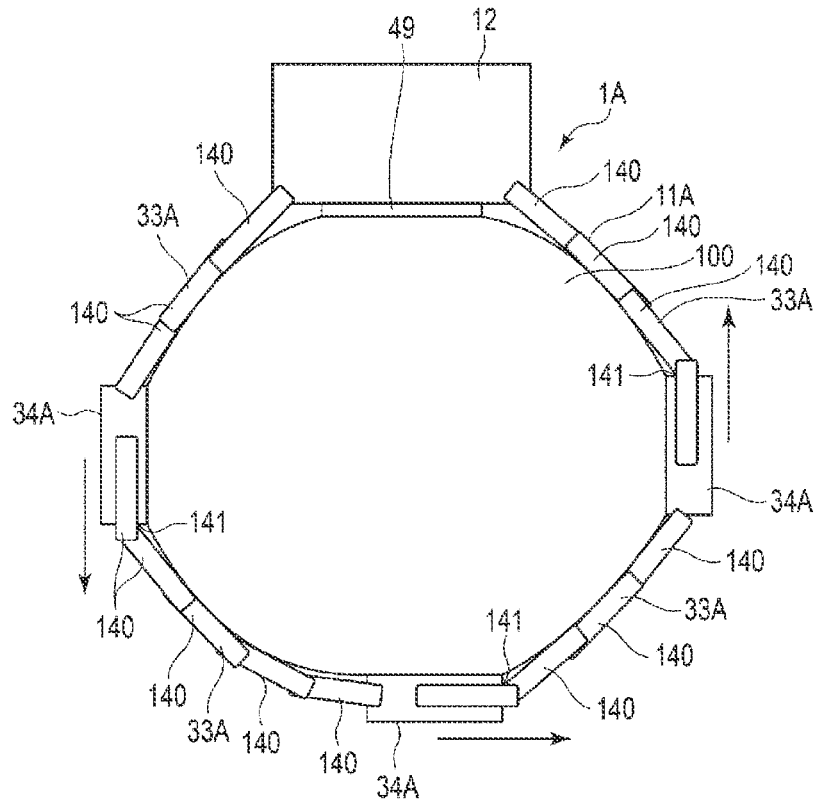
FIG. 12 is an explanatory view illustrating the configuration of an electrocardiographic measurement apparatus according to a second embodiment of the present invention.

An electrocardiographic measurement apparatus 1A according to a second embodiment of the present invention will be described with the use of FIG. 12. The same configurations as those in the first embodiment are denoted by the same reference numerals as those in the first embodi-ment, and descriptions thereof are omitted. FIG. 12 is an explanatory diagram illustrating a state where the electro-cardiographic measurement apparatus 1A is attached to the upper arm 100.

In the present embodiment, an example of the configu-ration will be described in which the plurality of electrodes that are brought into contact with the upper arm 100 to detect an electric potential of the upper arm 100 are configured such that the length of a portion projecting with respect to the reference position is variable and thus the length of the electrodes along the circumferential direction of the upper arm 100 is variable in accordance with the circumferential length of the upper arm 100.

As illustrated in FIG. 12, the electrocardiographic mea-surement apparatus 1A includes an attachment portion 11A that includes a plurality of electrodes 33A and is attached to the upper arm 100 with a portion of the upper arm 100 disposed inside the attachment portion 11A, and the device body 12 that generates electrocardiographic information based on electric potentials detected by the plurality of electrodes 33A.

The electrocardiographic measurement apparatus 1A functions as a so-called wearable device including the attachment portion 11A to be attached to the upper arm 100.

The attachment portion 11A is fixed to the device body 12 and is formed integrally with the device body 12 in a circular pattern. The attachment portion 11A is configured such that the upper arm 100 can be disposed inside the attachment portion 11A. The attachment portion 11A includes the plu-rality of electrodes 33A and a plurality of connecting por-tions 34A.

The electrode 33A is configured to be deformed, for example, along with the upper arm 100. For example, a plurality of electrode pieces 140 are connected, therefore forming the electrode 33A.

The connecting portion 34A is formed of an insulator. The connecting portion 34A insulates and connects the two electrodes 33A adjacent thereto. Also, the plurality of con-necting portions 34A each support one of the two electrodes 33A connected to the connecting portion 34A such that one of the two electrodes 33A can move forward and back with respect to the connecting portion 34A.

For example, a hole 141 in which a portion of the electrode 33 can be movably housed is formed in the connecting portion 34A. The plurality of electrodes 33A are configured such that the length of the portion projected from the hole 141 of the connecting portion 34A is variable, and thus the length of the electrodes 33A can vary along the circumferential direction of the upper arm 100. In such a configuration, the reference position is the edge of the hole 141.

Additionally, the connecting portion 34A is configured to be biased in a direction to pull the electrode 33A into the hole 141 when the electrode 33A is pulled in a direction to project from the hole 141. For example, an end portion of the electrode 33A, which is housed into hole of the connecting portion 34A is fixed to the hole of the connecting portion 34A by a spring. In addition, the spring expands and contracts, and thus the length of a portion of the electrode 33A, which is projected from the hole of the connecting portion 34A is variable.

According to the present embodiment, the effect similar to that of the first embodiment can be attained.

Note that in the aforementioned example, the configuration where the plurality of electrode pieces 140 are connected and thus the electrode 33A is formed is described as an example, but is not limited thereto. In another example, the electrode 33A may be a wire formed of a conductive material. In addition, a connecting portion 34D may be a code reel to which the wire-shaped electrode 33A is connected.

Third Embodiment

Figure 13:
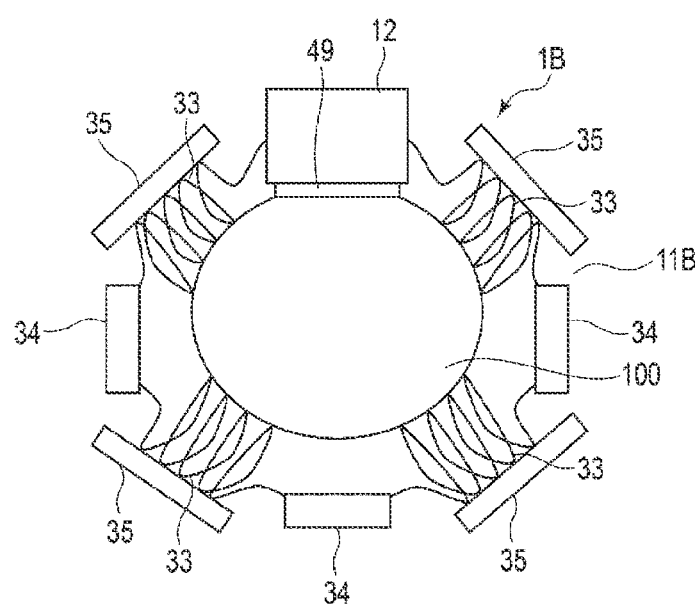
FIG. 13 is an explanatory view illustrating the configuration of an electrocardiographic measurement apparatus according to a third embodiment of the present invention.

Next, an electrocardiographic measurement apparatus 1B according to a third embodiment of the present invention will be described with the use of FIG. 13. The same configurations as those in the first embodiment are denoted by the same reference numerals as those in the first embodiment, and descriptions thereof are omitted. FIG. 13 is an explanatory diagram illustrating the configuration of the electrocardiographic measurement apparatus 1B.

The electrocardiographic measurement apparatus 1B includes an attachment portion 11B and the device body 12. The attachment portion 11B includes the plurality of electrodes 33, the plurality of connecting portions 34, and insulating portions 35. The insulating portions 35 are respectively disposed on the outer circumferential surface side of the plurality of electrodes 33 with the electrocardiographic measurement apparatus 1B attached to the upper arm 100. The insulating portion 35 covers a region of each of the plurality of electrodes 33, which does not contact the upper arm 100. The insulating portion 35 is formed of an insulator.

For example, a cover member formed of an insulator is fixed to each of the plurality of electrodes 33, and thus the insulating portion 35 is formed. Alternatively, an insulator is applied or plated to the electrode 33, and thus the insulating portion 35 may be formed.

According to the electrocardiographic measurement apparatus 1B configured as just described, the effect similar to that of the first embodiment can be attained. Additionally, at the time of measurement of an electric potential, the plurality of electrodes 33 can be prevented from being brought into contact with portions other than the upper arm 100 by the insulating portions 35. As a result, the measurement accuracy of the electric potential of the upper arm 100 by the electrocardiographic measurement apparatus 1B can be improved.

Fourth Embodiment

Figure 14:
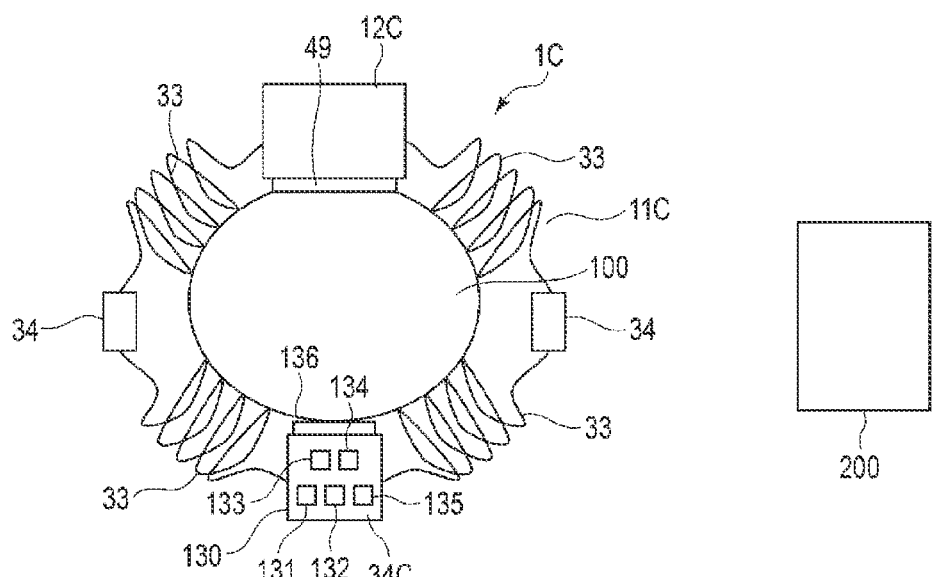
FIG. 14 is an explanatory view illustrating the configuration of an electrocardiographic measurement apparatus according to a fourth embodiment of the present invention.

Next, an electrocardiographic measurement apparatus 1C according to a fourth embodiment of the present invention will be described with the use of FIG. 14. Note that in the present embodiment, configurations similar to those of the first embodiment are denoted by the same reference numerals as those in the first embodiment, and descriptions thereof are omitted. FIG. 14 is an explanatory diagram illustrating the configuration of the electrocardiographic measurement apparatus 1C.

As illustrated in FIG. 14, the electrocardiographic measurement apparatus 1C includes an attachment portion 11C and a device body 12C.

The attachment portion 11C includes the plurality of electrodes 33, the plurality of connecting portions 34, and a sub-device body 130. Each of the plurality of electrodes 33 is fixed to the connecting portion 34, the device body 12C, or the sub-device body 130.

In the present embodiment, the plurality of connecting portions 34 are, for example, two connecting portions 34. The other ends of two of the electrodes 33, one ends of which are fixed to the device body 12C, are respectively fixed to the two connecting portions 34.

Two of the electrodes 33 are fixed to the sub-device body 130. The sub-device body 130 measures electric potentials of the two electrodes 33 fixed to the sub-device body 130. In addition, the sub-device body 130 generates electrocardiographic information based on the measured electric potentials and wirelessly transmits the generated electrocardiographic information to an external device 200. The external device 200 is, for example, a smart phone.

The sub-device body 130 includes, for example, a power supply unit 131, an electrocardiographic information generation unit 132, a signal transmission unit 133, a memory 134, and a control unit 135. Also, the sub-device body 130 includes a ground electrode 136.

The power supply unit 131 is a power source. The power supply unit 131 is, for example, a rechargeable battery such as a lithium ion battery. The power supply unit 131 is electrically connected to the control unit 135. As a specific example, the power supply unit 131 supplies power to the control unit 135. The power supply unit 131 supplies power for drive to the control unit 135, and via the control unit 135 to the electrocardiographic information generation unit 132, the signal transmission unit 133, and the memory 134.

The electrocardiographic information generation unit 132 is electrically connected to the two electrodes 33 fixed to the sub-device body 130, and the ground electrode 136. The electrocardiographic information generation unit 132 calculates a potential difference from electrical potentials detected by the two electrodes 33 and generates electrocardiographic information.

The electrocardiographic information generation unit 132 is, for example, a processing circuit that can execute functions of the electrocardiographic information generation unit 132. The electrocardiographic information generation unit 132 is electrically connected to the control unit 135. Note that the control unit 135 includes the processing circuit of the electrocardiographic information generation unit 132 and executes a program stored in the memory 134 and thus may perform the functions of the electrocardiographic information generation unit 132.

Also, for example, the electrocardiographic information generation unit 132 may include a low pass filter, an amplifier, and an analog/digital converter. For example, unnecessary noise components are removed from a signal of the potential difference by the low pass filter, and the signal is amplified by the amplifier and then converted into a digital signal by the analog/digital converter.

The signal transmission unit 133 is electrically connected to the electrocardiographic information generation unit 132. The signal transmission unit 133 wirelessly transmits the electrocardiographic information generated by the electrocardiographic information generation unit 132 to the external device 200.

The memory 134 includes a solid state drive (SSD), a random access memory (RAM), a read only memory (ROM), and the like. The memory 134 stores programs necessary for executing a variety of control processing. Additionally, the memory 134 stores the detected electrocardiographic signal and the generated electrocardiographic information. In addition, for example, the memory 134 stores these pieces of information in a chronological order.

The control unit 135 includes one or a plurality of processors. The control unit 135 is formed of one or more processing circuits. The control unit 135 is, for example, a central processing unit (CPU). The control unit 135 causes the entire operation and predetermined operation (function) of the electrocardiographic measurement apparatus 1C to be performed based on the programs stored in the memory 134. The control unit 135 executes the predetermined operation, analysis, processing, or the like according to the read program. The control unit 135 controls operation of the electrocardiographic information generation unit 132 and the signal transmission unit 133, transmits/receives a signal, and supplies power.

The ground electrode 136 is formed so as to be in contact with the upper arm 100 in a state where the electrocardiographic measurement apparatus 1C is attached to the upper arm 100.

The device body 12C calculates electric potentials of the two electrodes 33 fixed to the device body 12C, generates electrocardiographic information, and transmits the electrocardiographic information to the external device 200. The device body 12C includes, for example, a configuration other than the electrocardiogram generation unit 46 of the configuration of the device body 12 of the electrocardiographic measurement apparatus 1 according to the first embodiment, and a transmission unit. The device body 12C transmits information calculated by the electrocardiographic information generation unit 45 to the external device 200 by the transmission unit.

The external device 200 generates electrocardiogram information based on signals received from the device body 12C and the sub-device body 130. Also, the external device 200 may display an electrocardiogram based on the generated electrocardiographic information.

Note that the sub-device body 130 may be configured to transmit electrocardiographic information to the device body 12C. In this case, the device body 12C may be configured, for example, in the same manner as the device body 12 of the electrocardiographic measurement apparatus 1 according to the first embodiment. In addition, the electrocardiogram generation unit 46 of the device body 12C generates electrocardiogram information based on, for example, electrocardiographic information generated by the electrocardiographic information generation unit 45 and electrocardiographic information generated by the electrocardiographic information generation unit 132 of the sub-device body 130.

According to the electrocardiographic measurement apparatus 1C, the effect similar to that of the first embodiment can be attained. Further, the configuration where the electrocardiographic information is generated based on electric potentials detected by the plurality of electrodes 33 can be divided into the device body 12C and the sub-device body 130, and thus the device body 12C and the sub-device body 130 can be reduced in size.

Furthermore, since the electric potentials of the two electrodes 33 fixed to the sub-device body 130 are measured by the sub-device body 130, the two electrodes 33 are not electrically connected to the device body 12C. Therefore, wiring connected to the plurality of electrodes 33 can be simply routed.

Figure 15:
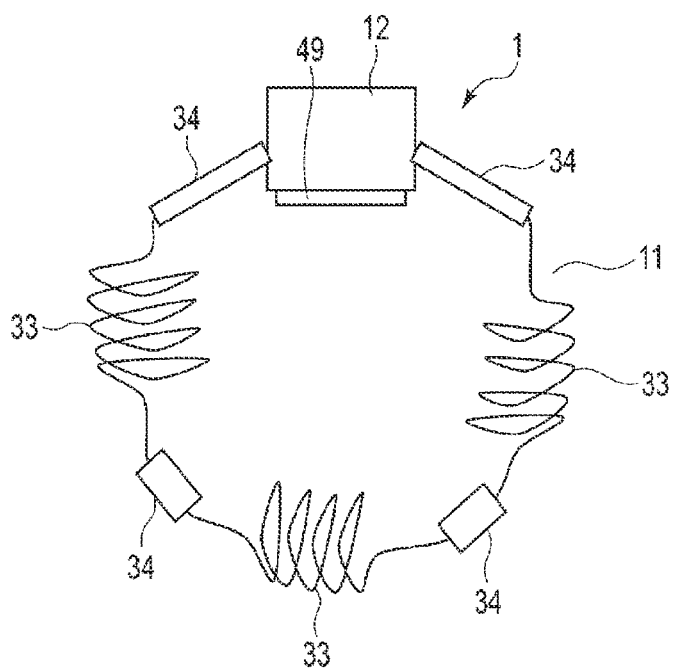
FIG. 15 is an explanatory view illustrating the configuration of the electrocardiographic measurement apparatus according to another embodiment of the present invention.

Note that in the aforementioned first to fourth embodiments, the configuration where the two electrodes 33 are fixed to the device body 12 is described as an example, but is not limited thereto. In other examples, as in a modified example of the electrocardiographic measurement apparatus 1 illustrated in FIG. 15, both ends of the attachment portion 11 may be formed of the two connecting portions 34. In addition, the two connecting portions 34 may be fixed to the device body 12.

Additionally, as a modified example of the first to fourth embodiments, one of the plurality of connecting portions 34 may be configured such that the length of the one connecting portion 34 along the circumferential direction of the upper arm 100 is adjustable to the extent that the plurality of electrodes 33 are maintained in the stretched state from the shortest length in a state where the electrocardiographic measurement apparatus 1, 1A, 1B, or 1C is attached to the upper arm 100. Such an example will be described as a modified example of the electrocardiographic measurement apparatus 1 of the first embodiment with the use of FIG. 16 and FIG. 17.

Figure 16:
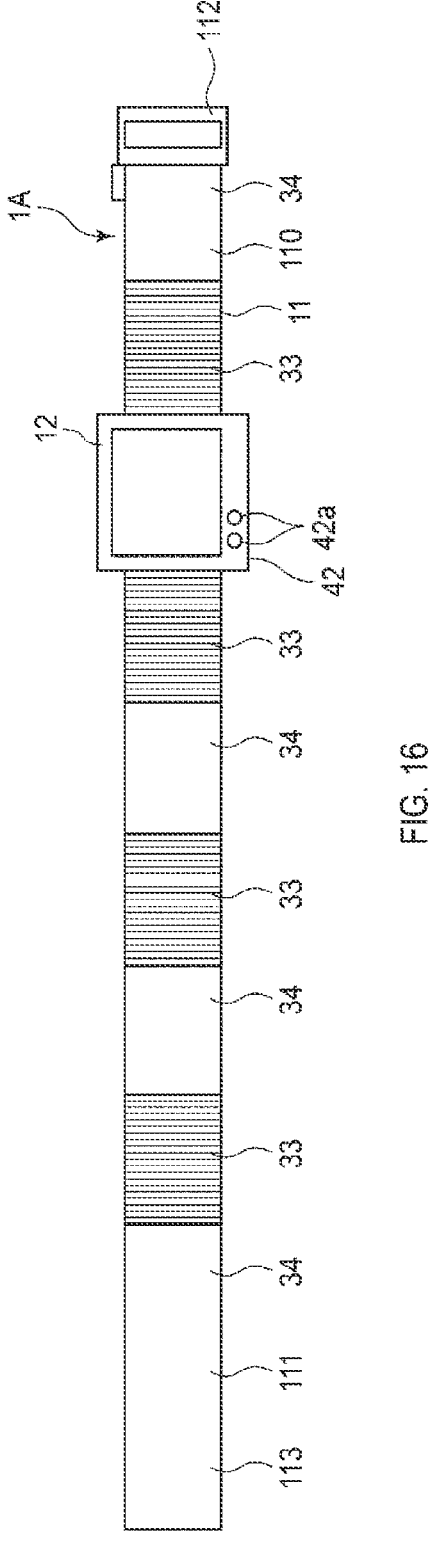
FIG. 16 is an explanatory diagram illustrating the configuration of the electrocardiographic measurement apparatus according to another embodiment of the present invention.
Figure 17:
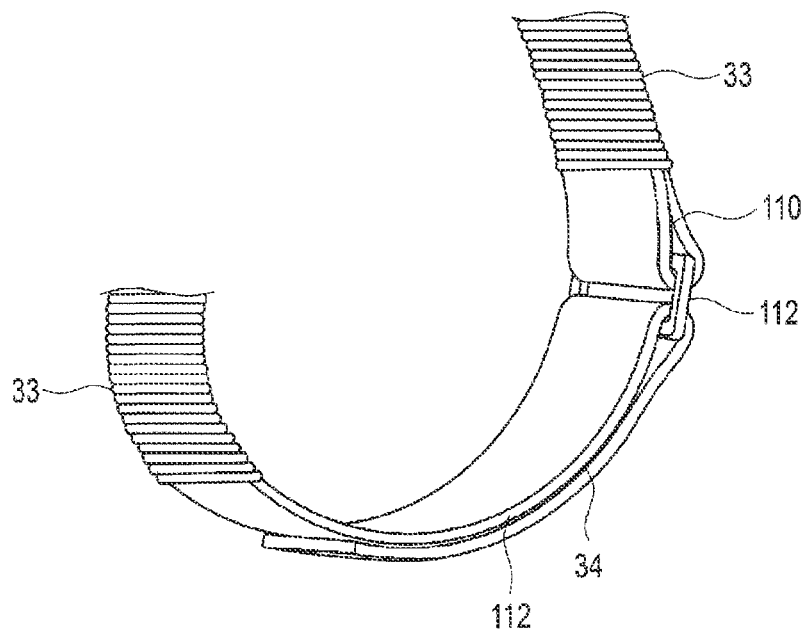
FIG. 17 is an explanatory diagram illustrating the configuration of a major portion of the electrocardiographic measurement apparatus; and, FIG. 18 is an explanatory diagram illustrating a state where the electrocardiographic measurement apparatus according to another embodiment of the present invention is attached to the upper arm.

As illustrated in FIG. 16 and FIG. 17, one connecting portion 34 of the plurality of connecting portions 34 is configured as a belt having an adjustable length. The one connecting portions 34 include, for example, a first portion 110, a second portion 111, and a fixing ring 112.

The first portion 110 is fixed, for example, to one of two adjacent electrodes 33. The second portion 111 is fixed to the other one of the two adjacent electrodes 33. The second portion 111 is formed in a strip shape. A hook-and-loop fastener 113 is disposed as an example of fixing means on the second portion 111. The hook-and-loop fastener 113 includes a hook and a loop. The fixing ring 112 is fixed to the first portion 110. The second portion 111 is folded back in the fixing ring 112 and fixed by the hook-and-loop fastener 113.

By adjusting the folding position of the second portion 111 in the fixing ring 112, the length of the connecting portion 34 can be adjusted. Additionally, the length of the connecting portion 34 can be adjusted to the extent that the plurality of electrodes 33 are maintained in the stretched state in a state where the electrocardiographic measurement apparatus 1 is fixed to the upper arm 100.

In other words, when the electrocardiographic measurement apparatus 1 is attached to the upper arm 100 having the shortest circumferential length of the upper arms 100 of the plurality of subjects set as a target for use of the electrocardiographic measurement apparatus 1 in a state where the length of the connecting portion 34 is longest, the plurality of electrodes 33 are maintained in the stretched state. Consequently, the electrocardiographic measurement apparatus 1 can be fixed to the upper arm 100 by fastening force due to the restoring force of the plurality of electrodes 33, and the tightening force can be adjusted by adjusting the length of the connecting portion 34. As a result, the electrocardiographic measurement apparatus 1 can be suitably fixed to the upper arm 100.

Additionally, in this modified example, one of the plurality of connecting portions 34 is configured in a belt shape, and thus the attachment portion 11 can be separated by this connecting portion 34. Accordingly, by separating the connecting portion 34 configured in a belt shape at the time of attaching the electrocardiographic measurement apparatus 1 to the upper arm 100, the attachment portion 11 and the device body 12 can be formed in a band shape. Consequently, the connecting portion 34 configured in a belt shape is connected in a state where the attachment portion 11 and the device body 12 that are in a band shape are wound around the upper arm 100, and thus the electrocardiographic measurement apparatus 1 can be fixed to the upper arm 100. As a result, operation for fixing the electrocardiographic measurement apparatus 1 to the upper arm 100 is easily performed.

Additionally, in the aforementioned example, the configuration where the device body 12 is fixed to the upper arm 100 by the attachment portion 11 with the use of the restoring force of the plurality of electrodes 33 is described as an example, but is not limited thereto. In another example, a fixture 160 that fixes the device body 12 to the upper arm may be disposed as in a modified example, illustrated in FIG. 18, of the electrocardiographic measurement apparatus 1 of the first embodiment.

Figure 18:
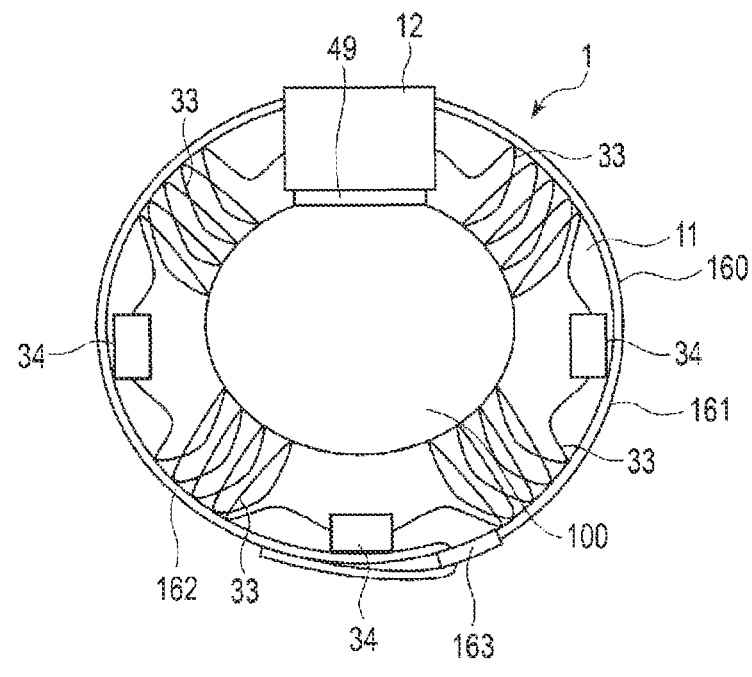

FIG. 18 is an explanatory diagram illustrating a state where the electrocardiographic measurement apparatus 1 of the modified example is attached to the upper arm 100. As illustrated in FIG. 18, the fixture 160 is disposed, for example, on the outside of the attachment portion 11 and is fixed to the device body 12. The fixture 160 is, for example, a belt.

The fixture 160 includes, for example, a first portion 161, a second portion 162, and a fixing ring 163. The first portion 161 is fixed to the device body 12. The second portion 162 is fixed to the device body 12. A hook-and-loop fastener is disposed as an example of fixing means on the second portion 162. The hook-and-loop fastener includes a hook and a loop. The fixing ring 163 is disposed at one end of the first portion 161.

A subject inserts the second portion 162 into the fixing ring 163, for example, after disposing the upper arm 100 within the attachment portion 11. Next, the subject folds back the second portion 162 in the fixing ring 163 and pulls the second portion 162. The second portion 162 is pulled, and thus the fixture 160 is tightened to the upper arm 100. At this time, the attachment portion 11 is also tightened to the upper arm 100 by the fixture 160.

For example, in a case where the plurality of electrodes 33 of the attachment portion 11 have no restoring force as illustrated in FIG. 6 and FIG. 7, the attachment portion 11 is tightened to the upper arm 100 by the fixture 160, and thus the length of the plurality of electrodes 33 contracts in accordance with the circumferential length of the upper arm 100. Therefore, the plurality of electrodes 33 are suitably brought into contact with the upper arm 100.

As just described, the electrocardiographic measurement apparatus 1 is fixed to the upper arm 100 by the fixture 160.

Additionally, in the aforementioned example, the configuration where the plurality of electrodes 33 are stretchable is described, but is not limited thereto. In other examples, in addition to the fact that the plurality of electrodes 33 are configured to be stretchable, at least one of the plurality of connecting portions 34 may be configured to be stretchable. As an example of such a configuration, at least one of the plurality of connecting portions 34 may be configured such that restoring force acts in a contracting direction from the stretched state. As a specific example, the connecting portion 34 may be formed in a coil shape. Alternatively, the connecting portion 34 may be configured in a bellows shape. Also, the connecting portion 34 may be configured to have no restoring force in a contracting direction from the stretched state, and as a specific example, the connecting portion 34 may include a link mechanism.

Further, in the aforementioned examples, the electrocardiographic measurement apparatus 1, 1A, 1B, or 1C is described with the use of an example in which the apparatus is attached to the upper arm 100, but may be configured to be attached to other portions of the living body such as a chest, a wrist, a leg, or the like.

Furthermore, in the aforementioned examples, an example of the configuration where the plurality of electrodes 33 are configured such that the length along the circumferential direction of the upper arm 100 is variable, but is not limited thereto. For example, at least one of the plurality of electrodes 33 may be configured such that the length of at least one of the plurality of electrodes 33 along the circumferential direction of the upper arm 100 is variable.

Additionally, in the aforementioned examples, the configuration where the attachment portion 11, 11A, 11B, or 11C is used for the electrocardiographic measurement apparatus 1 is described, but is not limited thereto. For example, the attachment portion 11 may be used in a biological information measurement device used for electrocardiographic measurement and blood pressure measurement. As a specific example, in addition to the configuration of the electrocardiographic measurement apparatus 1 described above, the biological information measurement device may include a processing circuit or the like that exerts a function of blood pressure measurement, which generates a blood pressure value from a pulse wave sensor and pulse wave information detected by the pulse wave sensor. Such a biological information measurement device calculates a pulse transit time (PTT) per heartbeat, and performs a function of blood pressure measurement that measures the blood pressure value by estimating blood pressure. Note that such a biological information measurement device calculates the pulse transit time (PTT) per heartbeat based on, for example, a time difference between an R-wave peak RP detected by an electrocardiographic signal and a pulse wave rise PS per heartbeat, which is one of the feature values of a pulse wave signal detected by the pulse wave sensor.

While the embodiments according to the present invention have been described in detail above, the above-described description merely exemplifies the present invention in all respects, and obviously, various improvements and modifications can be made without departing from the scope of the present invention. That is, specific configurations according to the respective embodiment may be employed as appropriate in the implementation of the present invention.

Additionally, in the present invention, various inventions can be formed by appropriately combining a plurality of components disclosed in the embodiments described above. For example, some components may be omitted from all the components described in the respective embodiments. Further, the components of the different embodiments may be combined appropriately.

REFERENCE NUMERALS LIST

1 Electrocardiographic measurement apparatus
1A Electrocardiographic measurement apparatus
1B Electrocardiographic measurement apparatus
1C Electrocardiographic measurement apparatus
1D Electrocardiographic measurement apparatus
11 Attachment portion 11A Attachment portion
11B Attachment portion
11C Attachment portion
11D Attachment portion
12 Device body
33 Electrode
33B Electrode
33D Electrode
34 Connecting portion
34A Connecting portion
34C Connecting portion
34D Connecting portion
35 Insulating portion
41 Case
42 Operation unit
42a Button
43 Display unit
44 Power supply unit
45 Electrocardiographic information generation unit
46 Electrocardiogram generation unit
47 Memory
48 Control unit
100 Upper arm
110 First portion
111 Second portion
112 Fixing ring
113 Hook-and-loop fastener
130 Sub-device body
131 Power supply unit
132 Electrocardiogram information generation unit
133 Signal transmission unit
140 Electrode piece
150 Plate member
160 Fixture
161 First portion
162 Second portion
163 Fixing ring

What is claimed is:

1. An electrocardiographic measurement apparatus, comprising:

a plurality of electrodes having a length adapted to be configured along a circumferential direction of a living body, the length being variable in accordance with a length in the circumferential direction of the living body, the plurality of electrodes being configured to detect an electric potential from the living body that is brought into contact with the plurality of electrodes; and a device body configured to generate electrocardiographic information based on the electric potential detected by the plurality of electrodes, wherein a projecting length from a reference position of each of the plurality of electrodes is variable, the reference position being a surface of a connecting portion to which the electrodes are fixed, wherein connecting portions are provided with a plurality of apertures or openings between connecting portions, and each of the plurality of electrodes projects from a respective one of the apertures or openings in the fixing member such that the projecting length of each electrode from the surface of the connecting portion is variable independent of any stretching of the connecting portion, and thus the length of the plurality of electrodes along the circumferential direction of the living body is variable.

2. The electrocardiographic measurement apparatus according to claim 1, wherein an outer circumferential surface side of each electrode of said plurality of electrodes is formed of an insulating portion.

3. The electrocardiographic measurement apparatus according to claim 1, wherein each of the plurality of electrodes is connected to an insulator, the device body, or a sub-device body to be configured in a circular pattern, and the sub-device body generates electrocardiographic information based on the electrical potential of the electrode connected to the sub-device body.

4. The electrocardiographic measurement apparatus according to claim 3, wherein the plurality of electrodes and the insulator, or the sub-device body to which each of the plurality of electrodes is connected, are configured to fix the device body to the living body.

* * * * *